United States Patent [19]

Maekawa

[11] Patent Number: 4,860,767

[45] Date of Patent: Aug. 29, 1989

[54] TOILET BOWL WITH HEALTH TESTING SYSTEM

[75] Inventor: Satosi Maekawa, Yokosuka, Japan

[73] Assignee: Maekawa Seisakujo Co., Ltd., Kanagawa, Japan

[21] Appl. No.: 180,788

[22] Filed: Apr. 12, 1988

[30] Foreign Application Priority Data

Apr. 14, 1987 [JP] Japan .................................. 62-89864

[51] Int. Cl.$^4$ .............................................. A61B 5/00
[52] U.S. Cl. .................................................. 128/760
[58] Field of Search ...................... 128/632, 760, 771; 73/864.21, 864.81–864.85

[56] References Cited

U.S. PATENT DOCUMENTS

| | | | |
|---|---|---|---|
| 3,625,654 | 12/1971 | Van Duyne | 128/760 |
| 4,137,573 | 2/1979 | Kroeger | 128/760 |
| 4,554,687 | 11/1985 | Carter et al. | 128/760 |

*Primary Examiner*—Max Hindenburg
*Attorney, Agent, or Firm*—L. Lawton Rogers, III; Joseph M. Killeen

[57] ABSTRACT

A toilet bowl with a health testing system of the present invention is characterized by comprising a portion for sampling specimens which is formed in an excreta-receiving portion of the toilet bowl, a test vessel which communicates with the sampling portion, to which a supply portion for supplying reagents or samples is connected and in which a sensor for detecting the condition of the specimen received in the vessel is provided, the sensor being connected to a conversion unit which codes the information obtained in the sensor and to which a comparison output unit for comparing the coded information supplied from the conversion unit with coded data and outputting the results of comparison is connected. Therefore, this toilet bowl system allows for automated sampling of urine and feces specimens from person's excreta on a daily basis so as to enable the automated assay of the specimens and diagnosis.

1 Claim, 2 Drawing Sheets

TOILET BOWL WITH HEALTH TESTING SYSTEM

BACKGROUND OF THE INVENTION

The present invention relates to a toilet bowl provided with an automated health testing system which comprises automated sampling of urine, automated diagnosis of the state of health of the person using the toilet bowl, and print-out of diagnostic records.

Most general toilet bowls only have the simple function of flushing away the excreta received therein and in some cases the function of providing for lavage of human organs.

On the other hand, a person's urine, feces or blood is collected when a diagnosis of the state of health of the person is made therefrom. However, for this purpose, it is necessary to collect urine or feces in vessels use exclusively for sampling which are individually prepared and to transfer the vessels to a place where the color, specific gravity, pH value, and presence of normal or abnormal substances can be assayed and diagnoses are made.

It is troublesome to collect blood or to collect urine and feces separately for the purpose of checking and diagnosis of the state of a person. In addition, a problem frequently occurs in that early detection of a disease is delayed due to the trouble of performing collection of blood, urine or feces.

SUMMARY OF THE INVENTION

The present invention has been achieved with a view to providing a toilet bowl system which allows for automated sampling of urine specimens from a person's excreta on a daily basis so as to enable the automated assay of the urine and diagnosis. This toilet bowl system is characterized by comprising a portion for sampling specimens which is formed in an excreta-receiving part of the bowl, a test vessel which communicates with the sampling portion and to which a supply portion for supplying reagents or samples is connected and in which a sensor for detecting the condiiton of the specimen received therein is provided, the sensor being connected to a conversion unit which codes the information obtained therein and to which a comparison output unit for comparing the coded information supplied from the conversion unit with the coded data and outputting the results of comparison is connected.

The excreta of a person are automatically sampled in the toilet bowl on a daily basis and then subjected to automated tests by appropriate analytical and test methods for the purpose of examining the excreta with respect to color, specific gravity, pH value, and presence of normal or abnormal substances, the state of health of the person then being diagnosed and the result of the diagnosis output.

DETAILED DESCRIPTION OF PREFERRED EMBODIMENTS

Embodiments of the present invention are described below with reference to the drawings.

Figure 1:
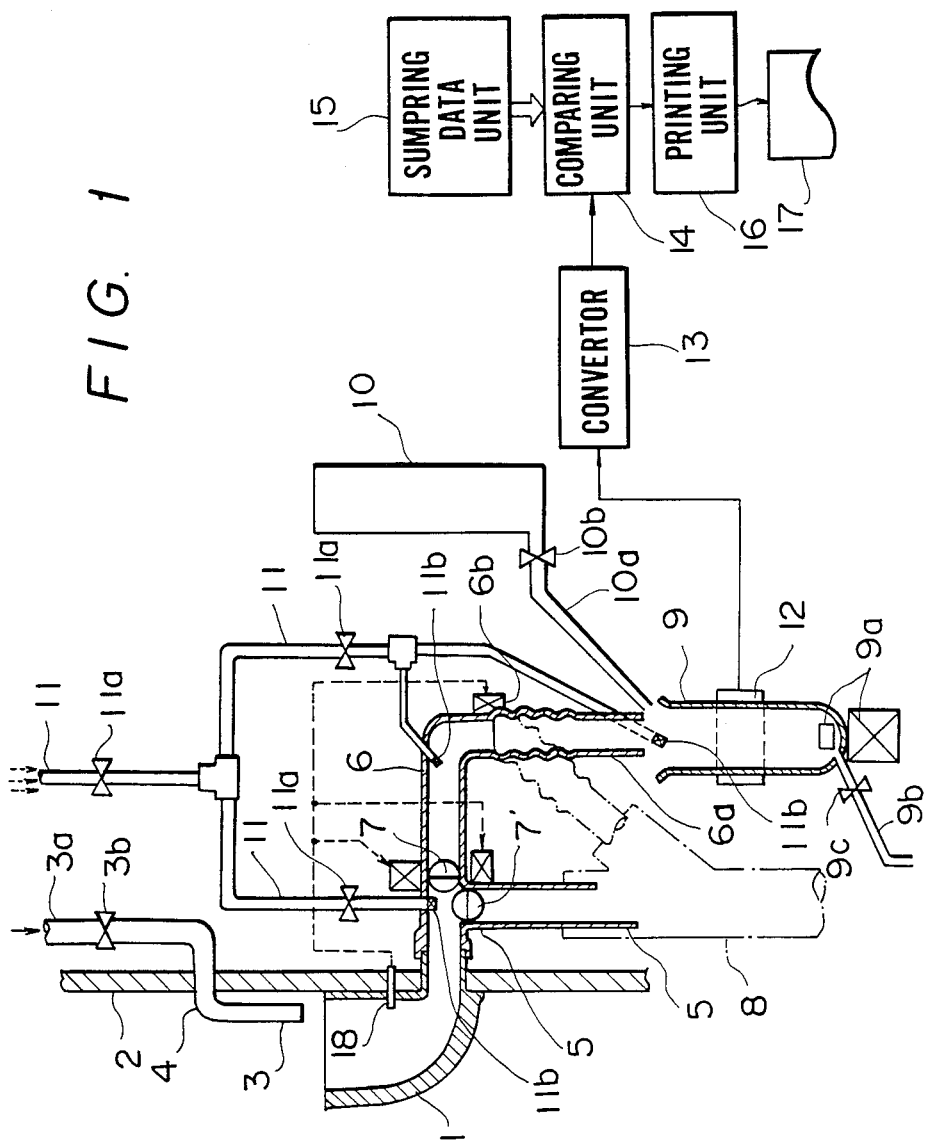
FIG. 1 is a systematic drawing of an embodiment of the toilet bowl system of the present invention.

FIG. 1 is a system drawing showing an outline of an embodiment of the toilet bowl system of the present invention. In this drawing, reference numeral 1 denotes a men's stall-type toilet bowl for urine; reference numeral 2, a wall to which the toilet bowl 1 is attached; reference numeral 3, a nozzle for flushing the toilet bowl; reference numeral 3a, piping with a valve 3b; reference numeral 4, flushing piping; and reference numeral 5, a drainage pipe. An example of general flush toilet bowls for urine comprises the members denoted by reference numerals 1 to 5. As a matter of course the present invention can also be applied to so-called Japanese-style toilet bowls and stool Western-style pedestal toilet bowls, as well as the above-described type of men's toilet bowl.

An embodiment of the toilet bowl system of the present invention has a configuration in which the members described below are added to the aforementioned toilet bowl.

In the embodiment, butterfly-type passage switch valves 7, 7' are provided in the drainage pipe 5, and reference numeral 6 denotes a sampling pipe which is formed at a position ahead of the valve 7 and has an end with a flexible pipe 6a that allows the direction of a flow of excreta to be changed from a direction for sampling to a direction for ordinary operation, vice versa.

Reference numeral 8 denotes a drainage pipe through which the ordinary passage of excreta takes place in a state wherein the flexible pipe 6a is placed in the position shown by the chain lines in the drawing.

Reference numeral 9 denotes a transparent test vessel having a test tube-like form to which urine specimens are supplied from the pipe 6a when the flexible pipe 6a is placed in the position shown by the solid lines in the drawing. The test vessel 9 is provided with a magnetic stirrer 9a and a drainage hole 9b having a valve 9c. A supply unit 10 for supplying the reagents described below and a supply pipe 11 having a valve 11a for supplying a washing liquid, disinfectant and so on are connected to the vessel 9.

Although not shown in the drawing, the sampling pipe 6 generally has a plurality of branches so as to make it possible to collect urine specimens in two or more test vessels 9. In this case, the flow is changed over from the drainage pipe 8 used for ordinary excreta to the sampling pipe 6 by opening and closing the switch valve 7 and the secondary switch valve 7' which is provided in front of the valve 7 in the drainage pipe (refer to FIG. 1).

The supply unit 10 for reagents is adapted to supply reagents for, for example, titration analyses through a supply pipe 10a to the test vessel 9 when a solenoid valve 10b provided in the supply pipe 10a and connected to the test vessel 9 is actuated. An example of a reagent that may be used in analyses is a solution consisting of a certain enzyme which is diluted to a concentration suitable for analyzing specimens.

Thus, when there are a plurality of test vessels 9, a corresponding number of reagent supply units 10 are provided in the system.

On the other hand, the supply pipe 11 for a washing liquid or disinfectant is arranged to supply the washing liquid to the test vessel 9, as well as to the sampling pipe 6 and the drainage pipe 5. Thus, the pipes 5, 6 and the vessel 9 are washed and disinfected each time urine passes through these pipes 5, 6 and the vessel 9.

During washing and disinfection, hot air and an air injection spray of a chemical may, for example, be applied to the pipes 5, 6 and the vessel 9 after this washing in order to dry and disinfect the same. Reference numeral 11b in the drawing denotes spray nozzles which are each provided at the end of a washing pipe for the purposes of washing and disinfection.

Reference numeral 12 denotes a sensor which is disposed such as to face the test vessel 9. An example of a sensor which may be provided in the system is a color discrimination sensor for detecting whether or not the color of urine in the test vessel 9 changes by titration with a given reagent and for detecting the degree of change.

In addition to the above-described color discrimination sensor, appropriate sensors may be used which can detect the presence of a reaction, the level of such reaction, or the presence of a particular substance, depending on the reagents which are added to the urine in the vessel 9 for the purpose of analyzing the urine and the results of the reaction. Analysis, reaction and detection may, for example, be undertaken on the following matters: specific gravity, pH value, sugar content, protein, bilirubin, ketone body, bromine, and uric acid, as well as the above-described color discrimination.

Reference numeral 13 denotes a converter which codes outputs from the sensor 12 and, for example, converts these outputs into a binary code and supplies the coded data to a subsequent comparator 14.

Reference numeral 15 denotes a data storage unit in which a plurality of sampling data to be compared with the coded data of the specimen are stored. A decision is made in the comparator 14 as to which sampling data is equivalent to the coded data with respect to the particular specimen which is supplied from the converter 13. When an item of sampling data is specified in the comparator 14, this data is converted into a common language signal and then output.

Reference numeral 16 denotes a printer which is driven by the output from the comparator 14 and prints the output signal thereof to show the result of the diagnosis of the urine specimen. Reference numeral 17 denotes the diagnosis paper print-out from the printer. The printing out may also be performed on a recording medium such as a magnetic card or an IC card.

The output of the comparator 14 may be supplied as data for another suitable computer. In this case, the output of the comparator 14 may be directly supplied to the computer or supplied to it through a recording medium such as a magnetic card or an IC card.

In the present invention, the apparatus consisting of the sensor 12 to the printer 16 represent an example of an automated diagnostic device for specimen samples provided by the toilet bowl system of the present invention. It is a matter of course that, when a plurality of test vessels are provided, a plurality of diagnostic unit systems would also be provided to correspond to the test vessels.

In the drawing, reference numeral 18 denotes a sensor for detecting an amount of urine to be tested which measures a sampling amount and supplies signals for controlling the opening and closing of the switch valves 7, 7' or the orientation of the flexible pipe 6a so as to prevent an excessive amount of urine from flowing into the sampling passage 6.

The toilet bowl 1 in the aforementioned embodiment is a men's stall-type toilet bowl for urine, but the present invention can also be applied to other types of toilet bowls.

A description will now be made of an example of application of the toilet bowl system of the above-described embodiment.

When a man urinates in the toilet bowl 1, urine is applied to the sampling amount sensor 18.

The sensor 18 causes the valve 7' to be closed in correspondence with a given previously-set time or amount, as well as causing the valve 7 to be opened, and supplies to a drive control unit 6a a signal to direct the flexible pipe 6a of the sampling pipe 6 to the test vessel 9.

When a given time has passed or a given amount of urine has been obtained, the valve 7 is closed and, at the same time, the valve 7' is opened, and the flexible pipe 6a is then directed to the drainage pipe 8 by the drive control unit 6b.

A given amount of a reagent is then dropped into the test vessel 9 from the supply pipe 10a. As a result, reaction takes place in the urine specimen.

This reaction is read out by the color discrimination sensor 12 in the above-described embodiment. Here, the color discrimination sensor 12 generates, for example, three types of electrical signals corresponding to the three primary colors and the intensities thereof. These signals are coded in the converter 13 and supplied to the comparator 14 in which they are compared with the sampling data stored in the storage unit 15, and the sampling data which is decided to be equivalent to the signal and which represents the result of diagnosis is output to the printer 16. The printer 16 prints out the diagnosis result and supplies it to the outside, whereby the person concerned can immediately can ascertain the state of his health.

In addition, such diagnostic results may be input as data for hospital out-patients or in-patients in the hospital computers.

When the present invention is applied to a pedestal-type Western-style toilet bowl, the members described below can be added to the arrangement of the present invention, thereby enabling an even more integrated automatic examination system.

A temperature sensor, pressure sensor, and heartbeat sensor may be provided on the toilet seat of a Western-style toilet bowl, and a processing unit which processes the detected values of each of the sensors is provided so that the body weight, body temperature, blood pressure and pulse of a person using the toilet bowl can be measured.

In this way, it is possible to record data that are used for precisely examining the state of health of a person in combination with the results of tests and analyses of urine performed in the above-described embodiment.

In addition, in a Western-style toilet bowl, feces may be sampled at the same time as urine. Thus, when the conditions (hardness and color, etc) of the sampled feces are examined and determined, all tests apart from blood tests can be conducted at the time of urination and defecation.

In this case, in order to sample urine and feces separately without their becoming mixed together, a sampling portion is configured in a manner such as that described below.

Figure 2:
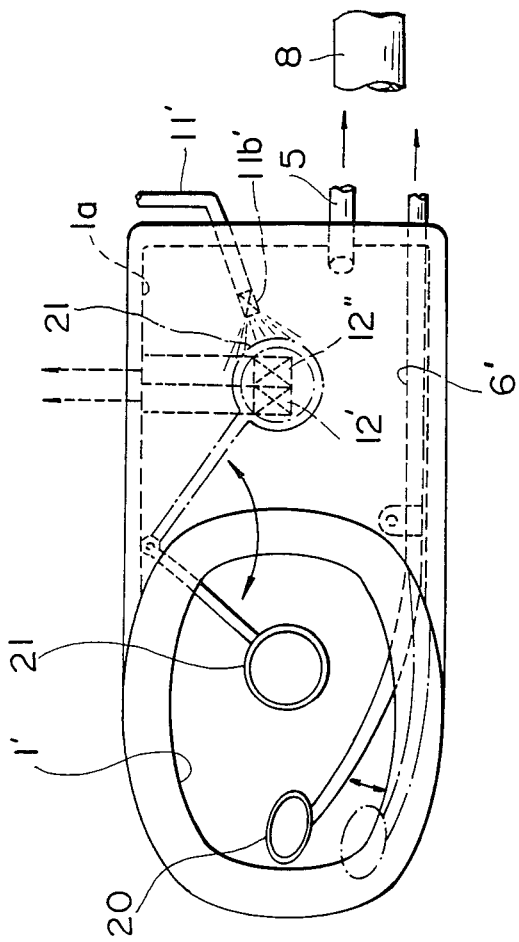
FIG. 2 is a plan view of another embodiment of the toilet bowl system.

As shown in FIG. 2, small sampling vessels 20, 21 are provided in a toilet bowl 1' in such a manner that they can be caused to appear or be retracted. In the example shown in FIG. 2, they are caused to advance or retreat by rotation and the urine and feces are separately collected in these vessels 20, 21.

The urine specimen collected is passed through a sampling passage 6' and introduced into the test vessel 9 where it is tested and analyzed in substantially the same manner as that employed in the first embodiment. The feces specimen collected in the vessel 21 which is then retracted into a rear chamber 1a where the color and hardness of the feces in the vessel 21 are automatically tested by testing means 12', 12" using a color sensor and pressure sensitive device. After the examinations have been carried out, the vessel 21 is washed with a liquid sprayed from a nozzle 11b' in the rear chamber 1a and is then dried and disinfected. At the same time, the feces in the vessel 21 are caused to pass down to the drainage pipe 8. Although not described in detail here, it is a matter of course that the vessel 20 is also washed, disinfected and dried.

As described above, since the present invention makes it possible to directly sample an urine specimen which is discharged in the daily life cycle of a person and diagnose the state of health on the basis of the urine specimen, the present invention is very useful as an automated examination system in a medical institution which is in an inconvenient placed from the viewpoints of prevention and early detection of disease or a place where many people have to be diagnosed.

In addition, if the toilet bowl system of the present invention is used in a hospital or a public health center, if the recorded data or the results of diagnoses are stored as computer data, for example, the necessary data with respect to either out-patients or in-patients can be automatically recorded. Thus the present invention greatly contributes to the automatic recording of diagnostic data in hospitals.

What is claimed is:

1. A toilet bowl with a health testing system characterized by comprising a portion for sampling specimens which is formed in an excreta-receiving portion of said toilet bowl, a test vessel which communicates with said sampling portion, to which a supply portion for supplying reagents or samples is connected and in which a sensor for detecting the condition of said specimen received in said vessel is provided, said sensor being connected to a conversion unit which codes the information obtained in said sensor and to which a comparison output unit for comparing the coded information supplied from said conversion unit with coded data and outputting the results of comparison is connected.

* * * * *